(12) United States Patent
Levin

(10) Patent No.: US 6,653,351 B2
(45) Date of Patent: Nov. 25, 2003

(54) ADJUVANT CHEMOTHERAPY FOR ANAPLASTIC GLIOMAS

(75) Inventor: Victor A. Levin, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/218,097

(22) Filed: Aug. 13, 2002

(65) Prior Publication Data

US 2003/0040526 A1 Feb. 27, 2003

Related U.S. Application Data

(60) Provisional application No. 60/311,914, filed on Aug. 13, 2001.

(51) Int. Cl.⁷ ............................................. A61K 31/195
(52) U.S. Cl. ....................................... 514/564; 514/283
(58) Field of Search ................................. 514/564, 283

(56) References Cited

U.S. PATENT DOCUMENTS

| | | | |
|---|---|---|---|
| 4,330,559 A | 5/1982 | Bey et al. | 424/319 |
| 4,413,141 A | 11/1983 | Bey et al. | 562/561 |
| 4,499,072 A | 2/1985 | Sunkara et al. | 424/85 |
| 4,818,770 A | 4/1989 | Weinstein et al. | 514/564 |
| 4,859,452 A | 8/1989 | Ajani et al. | 424/10 |
| 4,925,835 A | 5/1990 | Heston | 514/183 |
| 4,988,724 A | 1/1991 | Ajani et al. | 514/399 |
| 5,002,879 A | 3/1991 | Bowlin et al. | 435/71.1 |
| 5,162,373 A | 11/1992 | Ajani et al. | 514/564 |
| 5,189,025 A | 2/1993 | Ajani et al. | 514/23 |
| 5,851,537 A | 12/1998 | Alberts et al. | 424/400 |
| 6,083,496 A | 7/2000 | Poulin et al. | 424/78.27 |
| 6,166,079 A | 12/2000 | Follen et al. | 514/564 |

FOREIGN PATENT DOCUMENTS

| | | |
|---|---|---|
| WO | WO 98/14188 | 4/1998 |
| WO | WO 98/19667 | 5/1998 |
| WO | WO 98/25603 | 6/1998 |
| WO | WO 99/49859 | 10/1999 |
| WO | WO 00/69434 | 11/2000 |

OTHER PUBLICATIONS

Levin and Prados, "Treatment of reccurent gliomas and metastatic brain tumors with a polydrug protocol designed to combat nitrosourea resistance," *J. Clin. Oncol.*, 10(5):766–771, 1992.

Levin et al., "Phase III randomized study of postradiotherapy chemotherapy with α–difluoromethylornithine–procarbazine, N–(2–chloroethyl)–N'–cyclohexyl–N–nitrosurea, vincristine (DFMO–PCV) versus PCV for glioblastoma multiforme," *Clin. Cancer Res.*, 6(10):3878–3884, 2000.

Levin et al., "Radiation therapy and bromodeoxyuridine chemotherapy followed by procarbazine, lomustine, and vincristine for the treatment of anaplastic gliomas," *Int. J. Radiat. Oncol. Biol. Phys.*, 32(1):75–83, 1995.

Meyskens and Gerner, "Development of difluoromethylornithine as a chemoprevention agent for the management of colon cancer," *J. Cell Biochem. Suppl.*, 22:126–131, 1995.

Pasic et al., "α–difluoromethylornithine ototoxicity. Chemoprevention clinical trial results," *Arch. Otolaryngol Head Neck Surg.*, 123(12):1281–1286, 1997.

Prados et al., "Treatment of recurrent gliomas with 1,3–Bis(2–chloroethyl)–1–nitrosourea and α–difluoromethylornithine," *Neurosurgery*, 24(6):806–809, 1989.

Levin et al., "Phase III randomized study of post–irradiation chemotherapy wth DFMO–PCV versus PCV for anaplastic gliomas," *Proceedings: 93ʳᵈ Annual Meeting of the American Association for Cancer Research, San Francisco, CA,* Abstract # 2441, Apr. 6–10, 2002.

Levin, "Innovative adjuvant chemotherapy for patients with glioblastoma and anaplastic gliomas," Slides of the lecture presented at *M.D. Anderson Cancer Center Division of Cancer Medicine Grand Rounds*, Aug. 6, 2002.

Levin, "Phase III randomized study of post–radiation chemotherapy with DFMO–PCV versus PCV for anaplastic gliomas," Slides of the lecture presented at *M.D. Anderson Cancer Center, 13ᵗʰ Annual Community Clinical Oncology Program*, Mar. 9, 2002.

Levin, "Success with alpha–difluormethylornithine after 20 years!" Slides of the lecture presented at *M.D. Anderson Cancer Center Translation Research Seminar*, Jan. 11, 2002.

Yung, W. K. A. , "Chemotherapy for malignant brain tumors," *Cancer Bulletin*, 45/4:357–361, 1993.

*Primary Examiner*—James H Reamer
(74) *Attorney, Agent, or Firm*—Fulbright & Jaworski LLP

(57) ABSTRACT

The present invention provides a combination therapy using eflornithine (DFMO) and PCV (matulane, lomustine and vincristine) in the treatment of anaplastic gliomas. In contrast to the results seen with glioblastoma multiforme, anaplastic gliomas responded better to the combination of DFMO and PCV than to either the PCV combination or DFMO alone, extending patient survival by approximately two years.

33 Claims, 3 Drawing Sheets

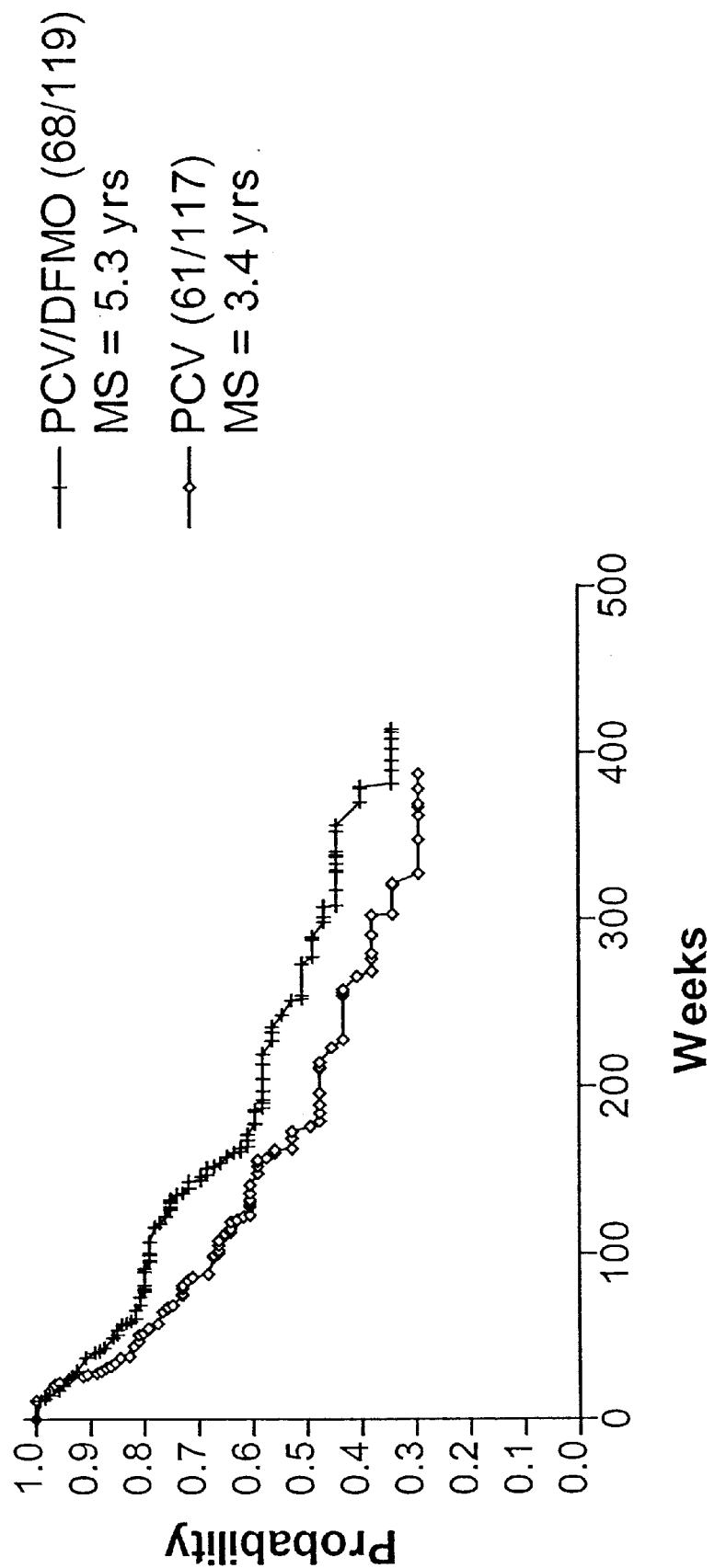
FIG. 1: DM92-035 PFS from registration for AA, AOA, AO, and MG

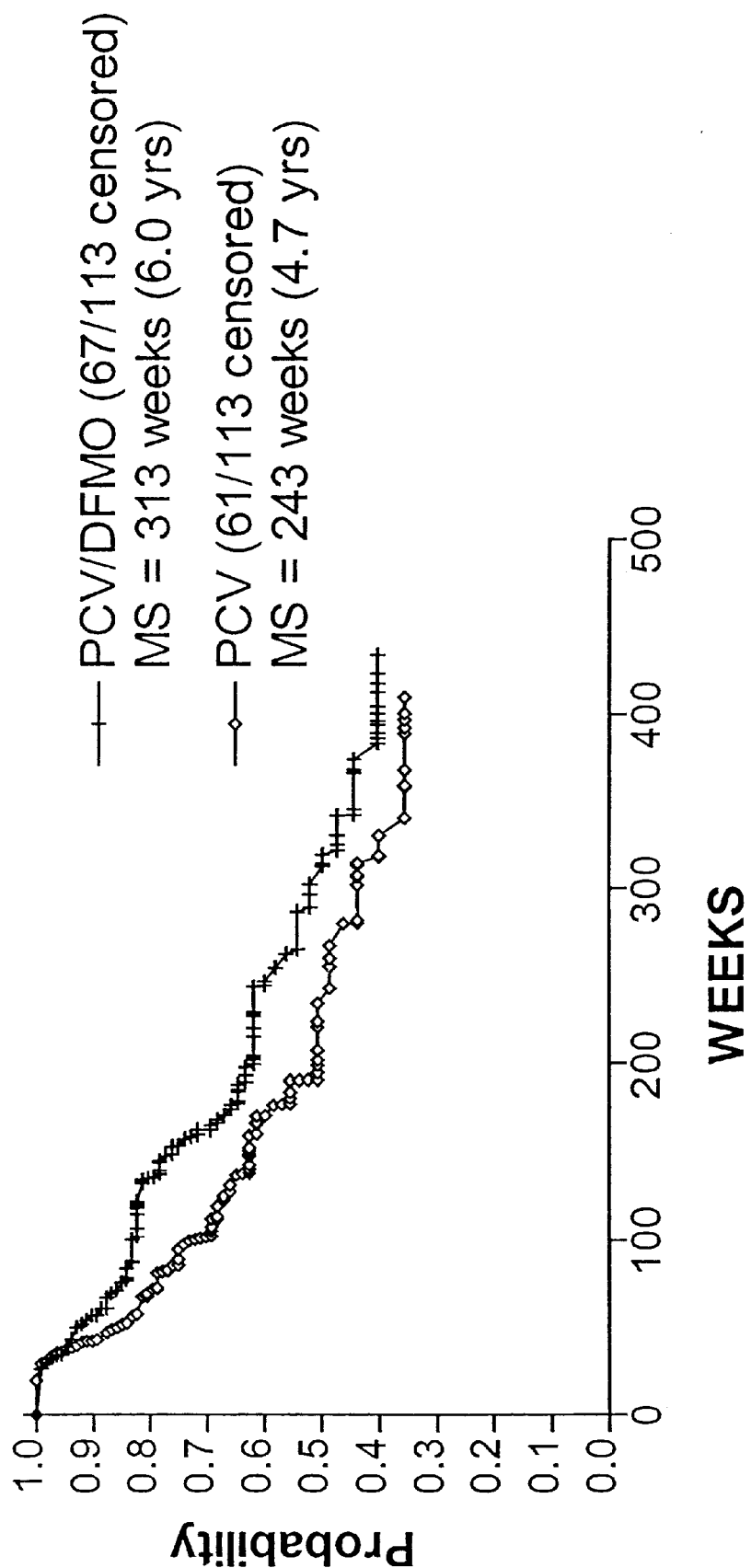

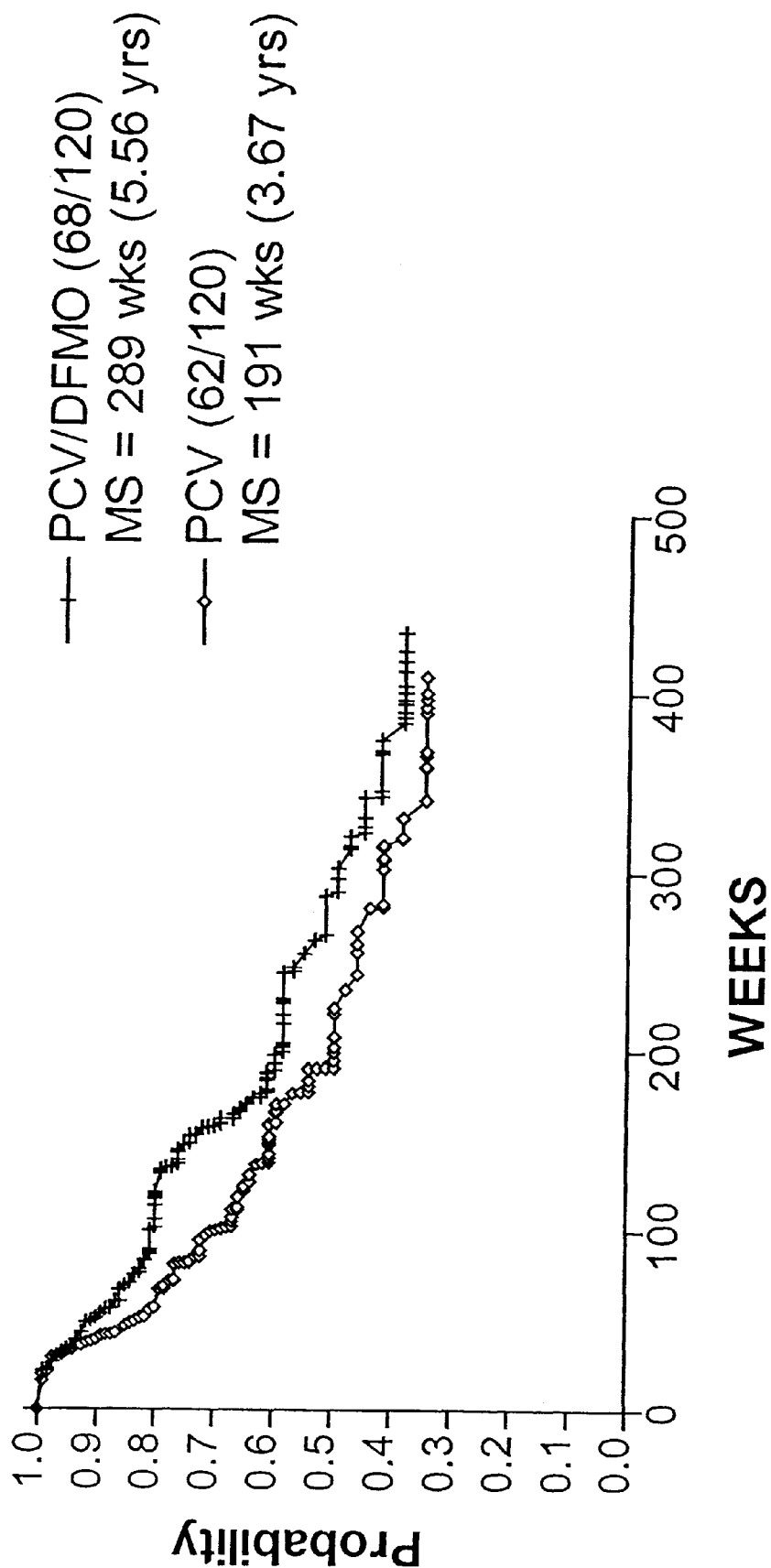
FIG. 3: DM92-035 Overall Survival Evaluable by Diagnosis and Treatment

ADJUVANT CHEMOTHERAPY FOR ANAPLASTIC GLIOMAS

This application is related to, and claims a benefit of priority from, copending provisional U.S. Provisional Ser. No. 60/311,914, filed Aug. 13, 2001, the entire contents of which are hereby expressly incorporated by reference for all purposes.

The government owns rights in the present invention pursuant to grant number CA55261 from the National Cancer Institute of the National Institutes of Health.

BACKGROUND OF THE INVENTION

1. Field of the Invention

The present invention relates generally to the fields of clinical cancer trials and chemopharmaceuticals. More particularly, it concerns the combined use of eflornithine, lomustine, matulane and vincristine for the treatment of anaplastic gliomas.

2. Description of Related Art

A. Gliomas

Gliomas are a diverse group of brain tumors that arise from normal "glial" cells of the brain and/or their precursor cells. The most important determinant of survival for gliomas is the "grade" of the glioma. Secondary determinants of survival are age at diagnosis, performance status, and extent of surgery. Patients with low-grade gliomas have a protracted natural history with generally long survival times, while those with high grade gliomas are much more difficult to successfully treat and have shorter survival times. All gliomas have specific signs and symptoms that are primarily related to the location and size of the glioma.

The temporal lobe gliomas, for example, may cause seizures, difficulty with speech and/or loss of memory. The frontal lobe gliomas may cause seizures, behavioral changes, weakness of the arms or legs on the opposite side of the body, and/or difficulty with speech. The occipital gliomas may cause loss of vision. The parietal gliomas may cause loss of spatial orientation, diminished sensation on the opposite side of the body, and/or inability to recognize once familiar objects or persons.

Astrocytomas are glioma tumors that arise from brain cells called astrocytes or their precursors. Astrocytes are cells in the central nervous system that support neuronal function. Astrocytomas can be graded by histologic features that signify increasing malignancy into astrocytoma, anaplastic astrocytoma, or glioblastoma multiforme. Anaplastic astrocytoma and glioblastoma multiforme are considered high-grade gliomas while the astrocytoma is considered to be a low-grade glioma. High-grade tumors grow rapidly and can easily infiltrate and spread through the brain. Low-grade astrocytomas can also infiltrate the brain but are usually more localized and grow slowly over a long period of time. High-grade tumors are much more aggressive and require very intense therapy. The majority of astrocytic tumors in children are low-grade, whereas the majority in adults are high-grade. Astrocytomas can occur anywhere in the brain and spinal cord, however the majority are located in the cerebral hemispheres (the top part of the brain).

Oligodendrogliomas are also gliomas. They arise from oligodendrocytes and/or their cell precursors. Normal oligodendrocytes provide myelin, a fatty substance that covers nerve axons in the brain and spinal cord and allows nerves to conduct electrical impulses more efficiently. Oligodendrogliomas are classified as low grade oligodendroglioma (less aggressive) and anaplastic oligodendroglioma (more aggressive). More common than pure oligodendrogliomas are low grade and anaplastic tumors that are a mixture of astrocytoma and oligodendroglioma ("oligoastrocytomas").

Anaplastic oligodendrogliomas and mixed oligoastrocytomas are more sensitive to cytotoxic chemotherapy than astrocytomas. A high rate of response to the PCV (procarbazine (matulane), CCNU (lomustine), vincristine) chemotherapy has made the use of this regimen, if not the standard of care for these tumors, at least a very common treatment. Additionally, low grade oligodendrogliomas are also sensitive to chemotherapy, and PCV can be used when low grade tumors begin to grow despite prior surgery and radiation therapy.

B. Chemotherapy

In 1983, it was reported that surgery plus radiation therapy and BCNU chemotherapy significantly improved the survival of patients with malignant glioma, as compared to those treated with surgery plus radiation therapy without chemotherapy. In one study, both procarbazine and streptozotocin demonstrated effectiveness similar to that of BCNU. Other studies showed that BCNU alone is as effective as BCNU followed by procarbazine, and that PCNU was no better than BCNU. In some studies the PCV combination was found superior to BCNU for anaplastic gliomas, while in other studies they are considered equivalent.

In addition to controlled survival-based clinical trials, a large number of agents have also been tested in response-based studies in glioma patients. To date, however, no drug has been found to be more effective than the nitrosoureas.

C. DFMO

Difluoromethylornithine (DFMO; eflornithine) is an irreversible inhibitor of ornithine decarboxylase (ODC), a key enzyme in mammalian polyamine biosynthesis (Pasic et al, 1997). Although the physiologic functions of polyamines are not completely understood, it is clear that their intracellular concentration is highly regulated and that normal cell growth, replication, differentiation, secretory and repair functions require polyamines (Pegg and McCann, 1982; Pegg, 1986; Bachrach et al., 1973; Williams-Ashman and Canellakis, 1979; Thet et al., 1984; Luk and Baylin, 1984). Polyamines have been found in high levels in many tumor cells (Pasic et al., 1997) and support sustained cell growth that is essential for the multistep process of cancer development. In animal models of colon carcinogenesis, inhibition of ODC by DFMO reduces the number and size of colon adenomas and carcinomas (Meyskens and Gemer, 1995). Elevated levels of ODC have also been reported in transitional cell carcinoma of the bladder and the use of DFMO as a treatment for bladder cancer patients has been reported (Messing et al., 1995).

DFMO and its use in the treatment of benign prostatic hypertrophy are described in two patents, U.S. Pat. Nos. 4,413,141, and 4,330,559. U.S. Pat. No. 4,413,141 describes DFMO as being a powerful inhibitor of ODC, both in vitro and in vivo. Administration of DFMO causes a decrease in putrescine and spermidine concentrations in cells in which these polyamines are normally actively produced. Additionally, DFMO has been shown to be capable of slowing neoplastic cell proliferation when tested in standard tumor models. U.S. Pat. No. 4,330,559 describes the use of DFMO and DFMO derivatives for the treatment of benign prostatic hypertrophy. Benign prostatic hypertrophy, like many disease states characterized by rapid cell proliferation, is accompanied by abnormal elevation of polyamine concentrations. The treatment described within this reference can be administered to a patient either orally, or parenterally.

Because DFMO is an effective inhibitor of ODC, some researchers are attempting to use DFMO as part of a conjunctive treatment in combination with other therapeutic agents. For instance, U.S. Pat. No. 4,499,072 describes improving the polyamine-depletion effects of ODC inhibitors (including DFMO) by using interferon in combination with the ODC inhibitor. Additionally, it describes the use of both an ODC inhibitor and interferon in conjunction with a known cytotoxic agent such as methotrexate. U.S. Pat. No. 5,002,879, describe a similar conjunctive therapy in which an ODC inhibitor, preferably DFMO, is used in combination with lymphokine-activated killer (LAK) cells and interleukin-2.

Despite advances in the art, there is a need for effective and improved therapies for anaplastic gliomas.

SUMMARY OF THE INVENTION

Thus, in accordance with the present invention, there is provided a method of treating anaplastic glioma in a subject comprising administering to said subject, in combined amount to effect treatment, a treatment regimen comprising at least one cycle of eflornithine, a hydrazine or triazine alkylating agent, preferably matulane, and a second alkylating agent, preferably a nitrosourea. The treatment may further comprise a tubulin interactive agent, preferably vincristine. Thus, the regimen may comprise eflornithine, matulane and a nitrosourea and, optionally, vincristine. The nitrosourea may be carmustine or, preferably, lomustine. In one aspect of the invention, the treatment regimen comprises at least one cycle of eflornithine, lomustine, matulane and vincristine administration, in combined amount to effect treatment. The treatment regimen may comprise administering eflornithine to said subject multiple times within said treatment cycle. The treatment regimen may also comprise administering eflornithine to said subject prior to or after lomustine, matulane or vincristine within said treatment cycle. The treatment regimen may comprise administering vincristine or matulane to said subject multiple times within said treatment cycle.

In one embodiment, the daily oral dose of eflornithine is about 9.0 g/m$^2$ given in three equal administrations each eight hours. In other embodiments the dose of eflornithine may be varied considering the treatment and condition of the subject. Such modifications of dosage are generally routine to one of skill in the art of clinical oncology. The forms of eflomithine include both isolated L-eflornithine and D-eflornithine, as well as a racemic mixture of L- and D-eflornithine. A higher dose of the D-form may be utilized, such as about 20 g/m$^2$, about 30 g/m$^2$, about 40 g/m$^2$, or about 50 g/m$^2$. The daily intravenous dose of vincristine is about 1.4 to about 2.0 mg/m$^2$. The daily oral dose of matulane is about 60 mg/m$^2$. The daily oral dose of lomustine is about 110 mg/m$^2$. The cycle may comprise: (a) eflornithine administered on days 1 to 14 and days 43 to 56; (b) lomustine administered on day 15; (c) matulane administered on days 22–35; and (d) vincristine administered on days 22 and 42. The cycle may be repeated at eight week intervals for a total of six or seven cycles. The doses of one or more of eflornithine, lomustine, matulane and vincristine may be modified after the first cycle.

The subject may have previously received radiation therapy, or may have previously received chemotherapy in addition to eflornithine, lomustine, matulane and vincristine, for example, hydroxyurea therapy (optionally including radiation therapy). The subject may be evaluated for neurotoxicity and ototoxicity after each cycle. The subject also may be is evaluated for blood count and platelet count during and after each cycle. The subject should have serum glutamic pyruvic transaminase and alkaline phosphatase less than or equal to two times normal values, total bilirubin less than or equal to 1.5 mg/dl, absolute neutrophil count of greater than or equal to 1500/mm$^3$ and platelet count of greater than or equal to 125,000/mm$^3$.

In another embodiment, there is provided a method of inhibiting the progression of anaplastic glioma in a subject comprising administering to said subject, in combined amount to effect treatment, a treatment regimen comprising at least one cycle of eflornithine, lomustine, matulane and vincristine administration. This treatment regimen may be provided after radiation therapy.

In yet another embodiment, there is provided a method of extending the life of a subject having anaplastic glioma comprising administering to said subject, in combined amount to effect treatment, a treatment regimen comprising at least one cycle of eflornithine, lomustine, matulane and vincristine administration. Again, the treatment regimen may be provided after radiation therapy.

In still yet another embodiment, there is provided a method of enhancing the effects of lomustine, matulane and vincristine on anaplastic glioma comprising administering to a patient having anaplastic glioma an amount of eflomithine sufficient to enhance the effects of lomustine, matulane and vincristine on said anaplastic glioma.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

TABLE 1—Patient Characteristics for Anaplastic Glioma Strata.

TABLE 2—Patient Characteristics for Anaplastic Glioma Strata.

TABLE 3—Patient Characteristics for Non-Evaluable Anaplastic Glioma Strata.

TABLE 4—Patient Characteristics for Best Evaluable Anaplastic Gliomas.

FIG. 1—DM92-035 progression-free survival (PFS) from Registration for AA, AOA, AO and MG.

FIG. 2—DM92-035 Overall Survival Evaluable AA, AOA, AO and MG.

FIG. 3—DM92-035 Overall Survival Evaluable by Diagnosis and Treatment.

DESCRIPTION OF ILLUSTRATIVE EMBODIMENTS

Gliomas are a complex family of brain tumors with different growth characteristics and involves different types of cells. Grading according to degree of malignancy was first proposed in 1949. In this classification, astrocytomas and glioblastomas represent different grades of malignancy of the same tumor. Grade I tumors, typically slow growing, are characterized by most cells having normal characteristics, and few mitotic features. Endothelial proliferation is absent. Grade II tumors, previously designated "astroblastomas," are characterized by an increased number of cells with polymorphic nuclei in mitoses. There is no clear line of demarcation from normal tissue. Grade III tumors represent anaplastic astrocytomas and Grade IV tumors represent the typical glioblastoma multiforme, characterized by cellular pleomorphism, vascular proliferation, mitoses, and multi-nucleated giant cells.

The current morphologically-based tumor classifications often mix cell lineage features with tumor growth characteristics. However, there are two general classifications—the anaplastic glioma strata and glioblastomas. The former is comprised of various gliomas including anaplastic astrocytomas, anaplastic oligoastrocytomas, anaplastic oligodendrogliomas, malignant glioma, anaplastic gliomas non-specified, and anaplastic ependymoma.

A recent report looked at the efficacy of the nitrosourea-based combination chemotherapy PCV (procarbazine, CCNU, and vincristine), used previously in treating intermediate grade (anaplastic) gliomas and glioblastoma, in the treatment of glioblastoma multiforme (Levin et al., 2000). In one aspect, the authors' protocol included α-difluoromethylornithine (DFMO), which had shown encouraging results in the setting of recurrent glioma patients, to PCV therapy. Following conventional radiation therapy, 272 glioblastoma (GBM) patients were randomized to receive either DFMO-PCV (134 patients) or PCV alone (138 patients), with survival and time to tumor progression being the primary endpoints. There was no difference in median survival or median time-to-tumor progression between the two treatment groups, as measured from day of commencement of postradiotherapy chemotherapy. Overall survival, as measured from time of tumor diagnosis at first surgery, was 13.3 and 14.2 months at the median and 6.2 and 8.7% at 5 years, respectively, for the DFMO-PCV and PCV arms. The treatment effect was unchanged after adjustment for age, performance status (KPS), extent of surgery, and other factors using the multivariate Cox proportional hazard model. Thus, the addition of DFMO to the nitrosourea-based PCV regimen in this phase III study demonstrated no additional benefit in glioblastoma patients, underscoring the resistance of glioblastoma multiforme tumors to alkylating agents.

1. The Present Invention

The present invention is directed to the use of DFMO-PCV in treating anaplastic gliomas and is based on and extends the study of Levin et al. (2000), in that, surprisingly, and in marked contrast to the results seen with glioblastoma multiforme, the combination of DFMO and PCV significantly increased the overall survival of patients with anaplastic gliomas. Particular aspects of the invention are discussed below in greater detail.

One common feature that may distinguish tumor response to DFMO is the level and activity of the enzyme ornithine decarboxylase (ODC). In glial tumors, ODC levels are directly related to malignancy grade (Scalabrino et al., 1982; Scalabrino and Ferioli 1985; Ernestus et al., 1992; Ernestus et al., 1996). Another neuroectodermal tumor, medulloblastoma, had even higher levels of ODC than the glial tumors (Scalabrino et al., 1982; Scalabrino and Ferioli 1985). A similar relationship to that of glial tumors has been seen also with adenocarcinomas of the breast (Glikman et al., 1987; Thomas et al., 1991; Manni et al., 1995; Manni et al., 1996; Mimori et al., 1998; Canizares et al., 1999), lung (Mohan et al., 1999), and colon (LaMuraglia et al., 1986; Berdinskikh et al., 1991). In the case of colon carcinoma, ODC is elevated in neoplastic tissues compared to normal colonic mucosa; however, there appears to be little difference in ODC levels from tumors of differing histological malignancy (Porter et al., 1987; Hietala et al., 1990; Takami et al., 1994).

When used in combination with nitrosourea alkylating agents, DFMO can increase antitumor activity in a variety of tumors studied in cell culture (Hung et al. 1981; Alhonen-Hongisto et al., 1984; Oredsson et al., 1984; Sano et al., 1984; Seidenfeld and Komar, 1985; Hunter et al., 1990; Sarkar et al., 1993) and in animals (Marton et al., 1981; Cohen et al, 1986). Similar studies in human clinical trials have been reported only for high-grade gliomas (Prados et al., 1989; Levin et al., 2000). It is likely that one factor that distinguishes DFMO benefit is the tumor level of GDC; patients with relatively lower levels of ODC appear to respond better to DFMO and DFMO-nitrosourea combinations. This conclusion is based on published observations that show that (1) ODC levels are directly correlated with malignant grade of glioma (Scalabrino et al., 1982; Scalabrino and Ferioli, 1985; Ernestus et al., 1992; Ernestus et al., 1996); (2) the fact that DFMO (+/−methylglyoxal bisguanylhydrazone) activity was not seen in glioblastoma multiforme and best seen in mid-grade anaplastic gliomas (Levin et al., 1987; Levin et al., 1992) with lower ODC levels; and (3) in combination with a nitrosourea, activity was not seen in glioblastoma multiforme and best seen in mid-grade anaplastic gliomas (Prados et al., 1989; Levin et al., 2000) with lower ODC levels. Thus, the inventor also anticipates a pattern of response in adenocarcinomas that show similar ODC relationships to malignant tumor grade, i.e., patients with low ODC levels will respond better (a longer more durable response) than those with higher ODC levels.

2. Anaplastic Glioma Strata

A. Clinical Features

The anaplastic gliomas are intermediate grade infiltrative gliomas—classified between low (localized, slow growing) and glioblastoma multiforme (rapidly growing and highly invasive). Anaplastic astrocytomas (AA) are tumors that arise from brain cells called astrocytes and/or their precursors. Astrocytes are support cells of the central nervous system. The majority of astrocytic tumors in children are low-grade, whereas the majority in adults are high-grade. These tumors can occur anywhere in the brain and spinal cord.

Oligodendrogliomas are gliomas derived from oligodendrocytes and/or their precursors. Oligodendrocytes that have a role in the structure and function of myclinated neurons in the brain. Anaplastic oligodendroglioma (AO) are more aggressive than oligodendrogliomas, but are also more sensitive to chemotherapy than are anaplastic astrocytomas. A high rate of response to the use of PCV (procarbazine, CCNU, vincristine) chemotherapy has led to the common use of PCV chemotherapy prior to radiation therapy, following irradiation, and/or at tumor recurrence and progression. Another glioma appears as histologic mixture of both oligodendroglioma and astrocytoma tumor forms and is called oligoastrocytoma. While oligoastrocytoma can be low-grade, the majority of the mixed oligoastrocytomas are anaplastic oligoastrocytomas (AOA).

The last glioma subgroup are ependymomas. One subtype of malignant ependymomas is the anaplastic ependymoma (AE); these tumors arise from ependymal cells and/or their precursors that line the cerebrospinal fluid passageways, called ventricles. These tumors are classified as either supratentorial (in the top part of the head) or infratentorial (in the back of the head).

Clinical features and symptoms produced by gliomas depend on the location of the tumor and the age of the patient. The most common location for gliomas is in the cerebral hemispheres in adults and the cerebellum, brainstem, hypothalamus, and thalamus in children. Spinal cord gliomas are much less common then gliomas of the brain. Patients with these tumors have symptoms that vary depending on location in the brain or spinal cord. They can produce symptoms of headache, seizures, nausea and vomiting, limb weakness, unilateral sensory changes, personality change, and unsteadiness in walking.

B. Classifications

Anaplastic Astrocytoma. The histologic features of anaplastic astrocytomas are similar to those of low-grade astrocytomas but these features are more abundant and exaggerated. These tumors are WHO grade III (Kleihues et al., 1993; Kleihues and Cavenee, 2000). Cellularity is more increased, as are nuclear and cellular pleomorphism. These features may be extreme, with back-to-back cells and bizarre, hyperchromatic nuclei. Cytoplasm may be scanty, with nuclear lobation and enlargement indicating anaplasia. Mitotic activity is easily recognized in most anaplastic astrocytomas but inexplicably may be absent in areas with gemistocytes.

The range of anaplasia in this grade is broad, with some examples showing low cellularity and pleomorphism with a few mitotic figures and others being highly cellular and pleomorphic with frequent mitoses, lacking only the necrosis required for a histologic diagnosis of glioblastoma. For this reason, it is useful to have a more objective indicator of behavior, and some markers of cell proliferation have been used in an attempt to predict prognosis more accurately. The most used markers in this area have been antibodies to bromodeoxyuridine (BrdU) and Ki-67 (Davis et al., 1995). The cellular incorporation of BrdU is a specific marker of the DNA synthesis phase of the cell cycle, whereas the Ki-67 antibody labels an antigen that is present in all phases of the cell cycle except $G_0$. Both antibodies can be identified by immunohistochemical staining in paraffin-embedded tissue sections. As a generalization, higher labeling rates for anaplastic astrocytomas is associated with poor prognosis (Hoshino et al., 1993; Davis et al., 1995; Lamborn et al., 1999).

Glioblastoma multiforme. Glioblastoma, also known as glioblastoma multiforme, is the glioma with the highest grade of malignancy, WHO grade IV (Kleihues and Cavenee, 2000). It represents 15% to 23% of intracranial tumors and about 50%–60% of astrocytomas. Most examples are generally considered to arise from astrocytes because glial fibrillary acidic protein can be identified in the cell cytoplasm. Some examples, however, apparently arise from other glial lineages, such as oligodendrocytes. Glioblastoma is the most frequently occurring astrocytoma. Autopsy and serial biopsy studies have shown that some astrocytomas progress through the grades of malignancy with transformation from low-grade to anaplastic astrocytoma to glioblastoma (Muller et al., 1977). But, because some examples of glioblastoma appear to arise rapidly in otherwise normal patients and are recognized when they are small, it is thought that this variety of glioblastoma can also arise directly from malignant transformation of astrocyte precursor cells without passing through the lower grades of malignancy (Kleihues and Ohgaki, 1997; 1999).

Tumor necrosis is the characteristic gross feature that distinguishes glioblastoma from anaplastic astrocytoma (Nelson et al., 1983; Burger et al., 1985; 1991). Another microscopic feature that is distinctive and diagnostic is the presence of proliferative vascular changes within the tumor. These changes may occur in the endothelial cells (vascular endothelial hyperplasia or proliferation) or in the cells of the vessel wall itself (vascular mural cell proliferation). Both types of change are sometimes considered together as microvascular proliferation. Glioblastomas cellularity is usually extremely high. The individual cells may be small, with a high nuclear:cytoplasmic ratio, or very large and bizarre, with abundant eosinophilic cytoplasm. These same small cells may appear to condense in rows around areas of tumor necrosis, forming the characteristic pseudopalisades. Glioblastoma tumors have a propensity to infiltrate the brain extensively, spreading even to distant locations and giving the appearance of a multifocal glioma. Some examples are truly multifocal (i.e., arising in multiple simultaneous primary sites) while many of these multifocal tumors show a histologic connection when the whole brain is examined at autopsy.

Oligodendrogliomas. Like astrocytomas, oligodendrogliomas mimic the histology of their presumed cell of origin. They also arise primarily in the white matter but tend to infiltrate the cerebral cortex more than do astrocytomas of a similar grade of malignancy. Like astrocytomas, grading schemes of histologic malignancy have been used for oligodendrogliomas, but these correlate less well with prognosis than those used for astrocytomas (Burger et al., 1987; Bigner et al., 1998; Daumas-Duport et al., 1997). Many of the histologic features used to grade oligodendrogliomas are similar to those used for astrocytomas: cellularity, pleomorphism, mitotic activity, vascular changes, and necrosis. Lower-grade oligodendrogliomas may have microcysts. Oligodendrogliomas of all histologic grades tend to infiltrate the cortex readily and to form clusters of neoplastic cells in the subpial region, around neurons, and around blood vessels. In general, the cells of oligodendrogliomas have round, regular nuclei and distinct cytoplasmic borders with clearing of the cytoplasm. Another fairly distinctive and diagnostically helpful feature is the vascular pattern of oligodendrogliomas, referred to as "chicken-wire" vessels that can divide the tumor into discrete lobules. With increasing anaplasia, oligodendrogliomas can become highly cellular and pleomorphic, approaching an appearance of glioblastoma multiforme with the presence of necrosis. Although it is correct to classify these as anaplastic oligodendrogliomas, some would use the term glioblastoma once necrosis is identified in any high-grade glial neoplasm. One justification for separating anaplastic oliogdendrogliomas from astrocytic glioblastomas is the slightly better prognosis of the former, even in this highest grade of malignancy. Some authors have reported that a MIB-1 labeling index of >3%–5% predicts a worse prognosis in oligodendrogliomas (Heegard et al., 1995; Kros et al., 1996; Dehghani et al., 1998).

Oligoastrocytomas. Many, if not most, oligodendrogliomas occur with a regional or intimate cellular mixture of astrocytoma. For the diagnosis of mixed glioma, the proportion of each should be substantial, but authors have differing opinions with respect to exact numbers; usually a mixture with a range from 10% to 25% of the minor element is used to diagnose a mixed glioma. Oligoastrocytomas and anaplastic oligoastrocytomas correspond to WHO grade II or grade III, respectively (Kleihues and Cavenee, 2000). Histologic features of anaplasia may be present in either component and will affect the prognosis adversely. Such features include marked cellular pleomorphism, high cellularity, and a high mitotic rate. Microvascular proliferation and necrosis may also be seen. Prognosis and response to therapy have not been shown to depend on the proportion of the oligodendroglial versus the astrocytic component (Shaw et al., 1994), although paradoxically, the BrdU LI of the oligodendroglial component is more predictive for survival than the astrocytic component (Wacker et al., 1994)

and far advanced tumor progressions are dominated by the astrocytic component.

3. PCV

PCV is a drug combination therapy employing three different agents—a hydrazine derivative, matulane, a nitrosourea, lomustine, and a tubulin interactive agent, vincristine. It has been used in a number of clinical trials, most notably by the inventor in assessing its effect on high-grade glioma and medulloblastoma tumors. The major side-effect observed with PCV was dose-limiting myelotoxicity. Each of the components of PCV is described below.

It should be noted that the present invention could include the use of BCNU rather than of CCNU (lomustine) since both are nitrosoureas. It also is contemplated that one could use CCNU and procarbazine or BCNU and procarbazine, without vincristine, since vincristine is usually considered to be the least active of the drugs in the PCV combination.

Both hydrazines and nitrosoureas are alkylating agents. As a group, alkylating agents form covalent chemical adducts with cellular DNA, RNA and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. In addition to hydrazine and nitrosoureas, aklyating agents include: triazenes such as dacarabzine and temozolomide, nitrogen mustards such as chlorambucil, cyclophosphamide, isofamide, mechlorethamine, melphalan, uracil mustard; aziridine such as thiotepa; methanesulphonate esters such as busulfan; platinum complexes such as cisplatin, carboplatin; bioreductive alkylators, such as mitomycin and and altretemine A. Hydrazine and Traizene Derivatives Hydrazine and triazene deriviatives are similar to nitrosoureas in that they decompose spontantously or are metabolized to produce alkyl carbonium ions, which alkylate DNA. This class of compounds includes matulane, dacarbazine and temozolomide.

The active ingredient in matulane is Procarbazine Hydrochloride (N-isopropl-alpha-(2-methylhydrazino)-p-toluamide monohydrochloride). It is available from Roche Laboratories, Inc. It was approved in 1969 for treatment of Hodgkins' Disease. The typical form is an oral capsule that contains 50 mg procarbazine as the hydrochloride. Dosages vary depending upon whether procarbazine is being used as a combination drug with other anticancer drugs or as a single therapeutic agent. A suggested guideline per the PDR for single agent use is 100 mg two times daily for 14 days.

The exact mode of actions of matulane is not clear. There is some evidence that the drug acts by inhibition of protein, RNA and DNA synthesis. It is primarily metabolized in the liver and kidneys and appears to be auto-oxidized to the azo derivative with the release of hydrogen peroxide. The azo derivative isomerizes to the hydrazone and, following hydrolysis, splits into a benzylaldehyde derivative and methylhydrazine. The methylhydrazine is further degraded to $CO_2$ and $CH_4$, and possibly hydrazine, whereas the aldehyde is oxidized to acid which is excreted in the urine.

Matulane exhibits monamine oxidase inhibitory activity (MAOI), so a diet that restricts foods which contain high tyramine content should be followed. Drugs to be avoided during therapy include antihistamines, sympathomimetics, barbiturates, narcotics, hypotensive agents or phenothiazines, and ethyl alcohol. Some foods are also to be avoided during procarbazine such as naturally aged cheeses, chocolates, nuts, and bananas as they could theoretcially lead to a hypertensive complication in some patients. Also, unacceptable toxicity may occur if matulane is used in patients with impairment of renal and/or hepatic function. Treatment may be curtailed in the event of central nervous system signs or symptoms such as paresthesias, neuropathies or confusion; neutropenia (absolute neutrophil count under 1500/ul), thrombocytopenia (platelets under 100,000/ul), hypersensitivity reaction, ulceraction or persistant spot of soreness around the oral cavity, diarrhea or loose stools, hemorrhage or bleeding tendencies.

Adverse but expected reactions include leukopenia, neutropenia, anemia, and thrombocytopenia. Commonly reported acute side effects are nausea and vomiting during or shortly after dose administration.

B. Nitrosoureas

Nitrosoureas represent a group of therapeutic alklyating agents. This class of compounds includes lomustine, carmustine, semustine, steptozocin, and nimustine.

(i) Lomustine

Lomustine is a synthetic akylating agent, also known as CCNU, with the chemical name of 1-(2-chloroethyl)-3-cyclohexyl-1-nitrosourea. It was approved in 1977 for treatment of brain tumors and Hodgkin's Disease. It is available from Bristol Myers Squibb as oral capsule, available in 10 mg, 40 mg and 100 mg forms. Dosages may vary depending upon whether lomustine is being used as a single agent or in a combination in addition to other chemotherapeutic agents. As a single agent in previously untreated patients, the recommended dosages per the PDR is 130 mg as a single oral dose every 6 weeks. Lomustine crosses the blood brain barrier.

It is believed that CCNU alkylates DNA and RNA. It is cross-resistant with other nitrosoureas and some but not all alkylating agents. It may also inhibit several key enzymatic processes by carbamoylation of amino acids in proteins.

The most common and severe toxic side effects are bone marrow suppression leading to thrombocytopenia and leukopenia, which may contribute to bleeding and infections. Bone marrow toxicity is cumulative and thus dosage adjustments must be considered on the basis of the nadir blood counts from prior doses.

(ii) Carmustine

Carmustine, also known as BCNU, with the chemical name of N,N'-Bis(2-chloroethyl)-N-nitrosurea, is a nitrosurea alkylating agent approved by the FDA in 1977. Carmustine has ben used for many years for treatment of primary brain tumors and is used for the treatment of gliomas. Carmustine is available from Bristol Meyers Squibb in packages containing vials of 10 mg carmustine and 3 ml sterile diluent for delivered by i.v. injection. As a single agent carmustine is administered at about 150–200 $mg/m^2$ every 6 weeks. In combination regimens, carmustine may be given in does similar to those of lomustine. An alternative mode of delivery is by wafers implanted directly into the tumor site (Gliadel® Wafer).

Potential side effects include bone marrow suppression, anemia, diarrhea, low white blood cell and platelet counts, pulmonary toxicity and swallowing difficulties.

C. Tubulin Interactive Agents

Tubulin interactive agents interfere with cell division by binding to specific sites on Tubulin, a protein that polymerizes to form cellular microtubules. Microtubules are critical cell structure units. When the interactive agents bind on the protein, the cell cannot properly form microtubules. Tubulin interactive agents include vincristine and vinblastine, both alkaloids and the taxanes, such as paclitaxel and docetaxel.

Vincristine, is available as Oncovin™ from Eli Lilly & Company and as Vincristine Sulfate from Faulding. Also called vincaleukoblastine, a 22-oxo-, sulfate (1:1) (salt), the salt of an alkaloid obtained from a common flowering herb, the perwinkle plant. It is delivered by intravenous injection. It was approved in 1963 on label for Ewing's Sarcoma, rhabdomyosarcoma, Wilm's Tumor, neuroblastoma. Hodgkin's Disease and leukemia.

The mechanism of action remains under investigation; however, there is an indication that inhibition of microtubule formation in the mitotic spindle, resulting in an arrest of dividing cells at the metaphase state, is involved. The liver is the major excretory organ. Most of an intravenous dose of Vincristine is escreted into the bile after rapid tissue binding. Vincristine does not appear to cross the blood brain barrier.

Vincristine has been reported to reduce blood levels of antiseizure medications and to increase seizure activity. The most common adverse reaction is hair loss. Leukopenia, neuritic pain and constipation occur, but usually for less than 7 days.

4. DFMO

Numerous highly proliferative types of cancer are associated with increased levels of the polyamines putrescine, spermidine, and spermine in tumor tissue and blood and urine of mammals with cancer. Studies have shown that this can be related to increased polyamine synthesis by the rate-limiting enzyme, omithine decarboxylase (ODC). The pathway for polyamine synthesis begins with L-omithine. This natural amino acid, although not normally incorporated into proteins, is part of the urea cycle which metabolizes arginine to omithine and urea. Omithine is converted by omithine decarboxylase (ODC) to putrescine and $CO_2$ and is considered to be the rate-limiting step in the production of polyamines. With the addition of propylamine donated from S-adenosylmethionine, putrescine is converted to spermidine. Spermidine is then converted to spermine by spermine synthetase, again in association with the decarboxylation of S-adenosylmethionine. Putrescine, spermidine and spermine represent the three major polyamines in mammalian tissues. Polyamines are found in animal tissues and microorganisms and are known to play an important role in cell growth and proliferation. Although the exact mechanism of the role of the polyamines in cell growth and proliferation is not known, it appears that the polyamines may facilitate macromolecular processes such as DNA, RNA, or protein synthesis. Polyamine levels are known to be high in the testes, ventral prostate, and thymus, in psoriatic skin lesions, and in other cells undergoing rapid growth processes.

It also is well known that the rapid proliferation of tumor tissue is marked by an abnormal elevation of polyamine levels. Hence, the polyamines also may play an important role in the maintenance of tumor growth. Thus, ODC inhibitors, such as DFMO, may exert their therapeutic effect by blocking the formation of the polyamines and thereby slowing, interrupting, or arresting the proliferation and metastases of the tumor tissue.

DFMO (alpha-difluoromethylomithine, eflornithine, Ornidyl®) is a structural analog of the amino acid L-omithine and has a chemical formula $C_6H_{12}N_2O_2F_2$. DFMO can be employed in the methods of the invention as a racemic (50/50) mixture of D- and L-enantiomers, or as a mixture of D- and L-isomers where the D-isomer is enriched relative to the L-isomer, for example, 70%, 80%, 90% or more by weight of the D-isomer relative to the L-isomer. The DFMO employed may also be substantially free of the L-enantiomer.

The dose limiting toxic effect of DFMO is thrombocytopenia (abnormally few platelets in the blood), which occurs in about fifty percent of patients, leukopenia (abnormally few leukocytes), or anemia. This toxic effect is relatively harmless and reversible and cease upon withdrawal of the drug.

The effect of an ODC inhibitor for the control of the growth rate of rapidly proliferating tumor tissue has been assessed in standard animal tumor models. For example, the anti-tumor effect of DFMO has been demonstrated in the following animal tumor models: L1210 leukemia in mice, EMT6 tumor in Balb/C mice, 7,12-dimethylbenzanthracene-induced (DMBA-induced) mammary tumor in rats, and DFMO Morris 7288C or 5123 hepatoma in Buffalo rats. In addition, the anti-tumor effect of DFMO in combination with various cytotoxic agents has been demonstrated as follows: (a) in combination with vindesine or adriamycin in L1210 leukemia in mice, in Morris 7288C hepatoma in Buffalo rats, and in EMT6 tumor in mice, (b) in combination with cytosine arabinoside in L1210 leukemia in mice, (c) in combination with methotrexate in L1210 leukemia in mice, (d) in combination with cyclophosphamide in EMT6 tumor in mice and in DMBA-induced tumor in mice, (e) in combination with BCNU in mouse glioma 26 brain tumor, and (f) in combination with MGBG in L1210 leukemia in mice, in Morris 7288C hepatoma in Buffalo rats, in P388 lymphocytic leukemia in mice, and in S-180 sarcoma in mice.

Although DFMO can effectively block tumor putrescine biosynthesis, the resultant antitumor effect is cytostasis, not cytotoxicity. For example, DFMO reduces the growth rate of an MCA sarcoma, but does not produce tumor regression. This finding is consistent with reports of other investigators who showed that DFMO is a cytostatic agent. However, studies indicate that a significant role may exist for DFMO agents, permitting the future development of combination chemotherapeutic regimens which incorporate DFMO.

The initial promise of DFMO as a therapeutic ODC inhibitor for use in the treatment of various neoplasias has dimmed somewhat because, although DFMO does, in fact, irreversibly inhibit ODC activity, cells treated in vivo with DFMO significantly increase their uptake of exogenous putrescine as described in U.S. Pat. No. 4,925,835. The intercellular transport mechanisms of the cell do an "end run" around the DFMO-impaired ODC activity by importing putrescine from the extracellular milieu. Therefore, DFMO's effect in vivo is far poorer than in vitro. So, while DFMO treatment effectively inhibits intracellular putrescine neogenesis, it also results in increased uptake of extracellular putrescine, thereby offsetting its ODC inhibitory effect.

This problem is compounded by the fact that putrescine is present in many common foods, such as grapefruit juice, which contains approximately 400 ppm putrescine. This makes it virtually impossible to provide a patient a nutritionally sufficient diet which is free of putrescine. Therefore, DFMO-treated cells are capable of importing sufficient amounts of extracellular putrescine to support cell division.

Strategies to make DFMO more acceptable to human patients are described in U.S. Pat. No. 4,859,452 (incorporated by reference). Formulations of DFMO are described which include essential amino acids in combination with either arginine or omithine to help reduce DFMO-induced toxicities.

5. Treatment Protocol

Thus, in accordance with the present invention, a therapeutic protocol using both DFMO and PCV therapy in the treatment of anaplastic gliomas is provided. Typically, the DFMO therapy will be provided prior and following the PCV therapy within a single cycle. However, it is contemplated that other orders will provide similar results. For example, DFMO is "A" and PCV is "B", the following are contemplated:

A/B/A B/A/B A/A/B B/A/A A/B/A/B
B/A/B/A A/A/AB B/A/A/A A/B/A/A A/A/B/A

In addition, it is contemplated that each DFMO/PCV cycle will be repeated one, two, three, four, five six, seven or more times. Also, as a general rule, lomustine is provided prior to either matulane or vincristine, but again, the order is not believed to be critical to the result. In certain cases it may be desirable to continue treatment with DFMO indefinitely after the first PCV cycle with the dosage of DFMO being adjusted to an adjuvant level, e.g., in the range of about 0.1 to about 3 g/m$^2$ BID.

The following is one example of a particular treatment protocol. A cycle constitutes 8 weeks (56 days). DFMO (3.0 g/m$^2$ oral every 8 hours) is administered on days 1–14 and 43–56. Lomustine (110 mg/m$^2$ oral) is administered on day 15. Matulane (60 mg/m$^2$/day oral) is administered on days 22–35. Vincristine (1.4 mg/m$^2$ i.v.) is administered on days 22 and 42. The cycle is repeated for a total of seven cycles, with breaks required for late nadir times and failure of blood counts to return to a "normal" within the allotted 56 day period of a treatment cycle.

Patients are evaluated by neurological examination during the study for neurological changes considered to be independent of tumor and graded using NCI Common Toxicity Criteria (neurotoxicity). Aside from baseline audiometric testing, repeat audiometric testing for ototoxicity is performed at the physician's discretion for patients who had evidence of hearing loss or progression of hearing loss by neurological examination. In addition, blood counts are performed biweekly, and serum creatinine, alkaline phosphatase, bilirubin and alanine amino-transferase tests are performed before each cycle. Doses may be modified during the course of treatment, primarily based on neutrophil and platelet counts (lomustine and matulane) or ototoxicity (DFMO). Occasionally, DFMO dose reductions are required for diarrhea.

6. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

DM92-035 Clinical Trial Parameters

Patients. Patients were enrolled for a multi-institutional phase III study at M.D. Anderson Cancer Center, the Metro-Minnesota Community Cancer Oncology Programs, and the University of California at San Francisco. Patients were stratified by histology into glioblastoma multiforme and anaplastic glioma, the latter being the subject of this trial. The demographics and cancer profile for patients is shown in TABLES 1–4.

DFMO+PCV Arm. A cycle constitutes 8 weeks (56 days). DFMO (3.0 g/m$^2$ oral every 8 hours) is administered on days 1–14 and 43–56. Lomustine (110 mg/m2 oral) is administered on day 15. Matulane (60 mg/m$^2$/day oral) is administered on days 22–35. Vincristine (1.4 mg/m$^2$ i.v.) is administered on days 22 and 42. The cycle is repeated for a total of six to seven cycles, with an occasional 1 or 2 week break between cycles for prolonged myelotoxicity.

PCV Arm. A cycle constitutes 6 weeks (48 days). Lomustine (110 mg/m$^2$ oral) is administered on day 1. Matulane (60 mg/m$^2$/day oral) is administered on days 8–21. Vincristine (1.4 mg/m$^2$ i.v.) is administered on days 8 and 29. The cycle is repeated for a total of six to seven cycles, with an occasional 1 or 2 week break between cycles for prolonged myelotoxicity.

Example 2

DM92-035 Clinical Trial Results

The results of the study are reported in FIGS. 1–3. FIG. 1 shows a comparison of PCV versus DFMO+PCV for anaplastic astrocytomas (AA), anaplastic oliogoastrocytomas (AOA) and anaplastic oliogodendrogliomas (AO), as well as malignant glioma not otherwise specified (MG). As illustrated in this "intent to treat" analysis of 236 patients the combined results show an improvement in progression-free survival (PFS) from study registration of 3.4 years for PCV to 5.3 years for DFMO+PCV. FIG. 2, shows improved overall survival from date of surgical diagnosis for the same set of cancers in 226 patients that were considered to be fully evaluable for response based on treatment in that they actually received the prescribed therapy for at least 2 weeks. For this fully evaluable group, median survival increased from 4.7 years for PCV to 6.0 years for DFMO+PCV. FIG. 3 illustrates a similar result for overall survival using an "intent to treat" analysis for all patients evaluable by diagnosis and treatment with 3.67 years for PCV and 5.56 years for the PCV+DFMO combination.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,330,559
U.S. Pat. No. 4,413,141
U.S. Pat. No. 4,499,072
U.S. Pat. No. 4,859,452
U.S. Pat. No. 4,925,835
U.S. Pat. No. 5,002,879
Alhonen-Hongisto, Deen, Marton, "Time dependence of the potentiation of 1,3-bis(2-chloroethyl)-1-nitrosourea cytotoxicity caused by alpha-difluoromethylornithine-induced polyamine depletion in 9L rat brain tumor cells," *Cancer Res.*, 44(5):1819–1822, 1984.

Bachrach, Don, Wiener, "Polyamines and tumor cells: effect of transformation of chick embryo fibroblasts by Rous sarcoma virus on polyamine levels," *Biochem. Biophys. Res. Commun.*, 55(3):1035–1041, 1973.

Berdinskikh, Ignatenko, Zaletok, Ganina, Chomiy, "Ornithine decarboxylase activity and polyamine content in adenocarcinomas of human stomach and large intestine," *Int. J. Cancer*, 47(4):496–498, 1991.

Bigner, McLendon, Bruner, In: *Pathology of Tumors of the Nervous System*, Russell and Rubinstein (Eds.), 6th Edition, London:Edward Arnold, p. 757, 1998.

Burger, Rawlings, Cox, McLendon, Schold, Bullard, "Clinicopathologic correlations in the oligodendroglioma," *Cancer*, 59:1345–1352, 1987.

Burger, Scheithauer, Vogel, In: *Surgical Pathology of the Nervous System and Its Coverings*, $3^{rd}$ ed., New York, Churchill Livingstone, Inc, p. 737, 1991.

Burger, Vogel, Green, Strike, "Glioblastoma multiforme and anaplastic astrocytoma. Pathologic criteria and prognostic implications, *Cancer*, 56:1106–1111, 1985.

Canizares, Salinas, de las Heras, Diaz, Tovar, Martinez, Penafiel, "Prognostic value of ornithine decarboxylase and polyamines in human breast cancer: correlation with clinicopathologic parameters," *Clin. Cancer Res.*, 5(8): 2035–2041, 1999.

Cohen, Pietronigro, Cravioto, Flamm, Effect of difluoromethylomithine on the antiglioma therapeutic efficacy of intra-arterial BCNU," *J. Neurosurg.*, 65(5):671–678, 1986.

Daumas-Duport, Tucker, Kolles et al., "Oligodendrogliomas. Part II: A new grading system based on morphological and imaging criteria," *J. Neurooncol.*, 34:61–78, 1997.

Davis, Onda, Shubuya, Lamborn, Hoshino, "Proliferation markers in gliomas: a comparison of BUDR, KI-67, and MIB-1," *J Neurooncol.*, 24:9–12, 1995.

Dehghani, Schachenmayr, Laun, Krof, "Prognostic implication of histopathological, immunohistochemical and clinical features of oligodendrogliomas: a study of 89 cases," *Acta Neuropathol*, 95:493–504, 1998.

Ernestus, Rohn, Schroder, Els, Lee, Klug, Paschen, "Polyamine metabolism in gliomas," *J. Neurooncol.*, 29(2): 167–174, 1996.

Ernestus, Rohn, Schroder, Klug, Hossmann, Paschen, "Activity of ornithine decarboxylase (ODC) and polyamine levels as biochemical markers of malignancy in human brain tumors," *Acta. Histochem. Suppl.*, 42:159–164, 1992.

Glikman, Vegh, Pollina, Mosto, Levy, "Ornithine decarboxylase activity, prolactin blood levels, and estradiol and progesterone receptors in human breast cancer," *Cancer*, 60(9):2237–2243, 1987.

Heegard, Sommer, Broholm, Broendstrup, "Proliferating cell nuclear antigen and Ki-67 immunohistochemistry of oligodendrogliomas with special reference to prognosis," *Cancer*, 76:1809–1813, 1995.

Hietala, Yum, Pilon, O'Donnell, Holroyde, Kline, Reichard, Litwin, Gilmour, O'Brien, "Properties of ornithine decarboxylase in human colorectal adenocarcinomas," *Cancer Res.*, 50(7):2088–2094, 1990.

Hoshino, Ahn, Prados, Lamborn, Wilson, "Prognostic significance of the proliferative potential of intracranial gliomas measured by bromodeoxyuridine labeling," *Int. J Cancer*, 53:550–555, 1993.

Hung, Deen, Seidenfeld, Marton, "Sensitization of 9L rat brain gliosarcoma cells to 1,3-bis(2-chloroethyl)-1-nitrosourea by alpha-difluoromethylomithine, an ornithine decarboxylase inhibitor," *Cancer Res.*, 41(7):2783–2785, 1981.

Hunter, Deen, Pellarin, Marton, "Effect of alpha-difluoromethylornithine on 1,3-bis(2-chloroethyl)-1-nitrosourea and cis-diamminedichloroplatinum(II) cytotoxicity, DNA interstrand cross-linking, and growth in human brain tumor cell lines in vitro," *Cancer Res.*, 50(9): 2769–2772, 1990.

Kleihues and Cavenee, "Pathology and Genetics of Tumors of the Nervous System," IARC Press, Lyon, 227–228, 2000.

Kleihues and Ohgaki, "Genetics of glioma progression and the definition of primary and secondary glioblastoma," *Brain Pathol*, 7:1131–1136, 1997.

Kleihues and Ohgaki, "Primary and secondary glioblastoma: from concept to clinical diagnosis," *Neuro-Oncology*, 1:44–51, 1999.

Kleihues, Burger, Scheithauer, In: *Histological Typing of Tumours of the Central Nervous System*, 2d ed., Berlin: Springer-Verlag, 112 p., 1993.

Kros, Hop, Godschalk, Krishnadath, "Prognostic value of the proliferation-related antigen Ki-67 in oligodendrogliomas," *Cancer*, 78:1107–1113, 1996.

Lamborn, Prados, Kaplan, Davis, "Final report on the University of California San Francisco experience with bromodeoxyuridine labeling index as a prognostic factor for the survival of glioma patients," *Cancer*, 85:925–935, 1999.

LaMuraglia, Lacaine, Malt, "High omithine decarboxylase activity and polyamine levels in human colorectal neoplasia," *Ann. Surg.*, 204(1):89–93, 1986.

Levin and Prados, "Treatment of recurrent gliomas and metastatic brain tumors with a polydrug protocol designed to combat nitrosourea resistance," *J. Clin. Oncol.*, 10(5): 766–71, 1992.

Levin, Prados, Wara, Davis, Gutin, Phillips, Lamborn, Wilson, "Radiation therapy and bromodeoxyuridine chemotherapy followed by procarbazine, lomustine, and vincristine for the treatment of anaplastic gliomas," *Int. J. Radiat. Oncol. Biol. Phys.*, 32(1):75–83, 1995.

Levin, Uhm, Jaeckle, Choucair, Flynn, Yung, Prados, Bruner, Chang, Kyritsis, Gleason, Hess, "Phase III randomized study of postradiotherapy chemotherapy with alpha-difluoromethylornithine-procarbazine, N-(2-chloroethyl)-N'-cyclohexyl-N-nitrosurea, vincristine (DFMO-PCV) versus PCV for glioblastoma multiforme," *Clin. Cancer Res.*, 6(10):3878–3884, 2000.

Luk and Baylin, "Ornithine decarboxylase as a biologic marker in familial colonic polyposis," *N. Engl. J Med.*, 311(2):80–83, 1984.

Manni, Mauger, Gimotty, Badger, "Prognostic influence on survival of increased ornithine decarboxylase activity in human breast cancer," *Clin. Cancer Res.*, 2(11):1901–1906, 1996.

Manni, Wechter, Wei, Heitjan, Demers, "Phenotypic features of breast cancer cells overexpressing ornithine-decarboxylase," *J. Cell Physiol.*, 163(1):129–136, 1995.

Marton, Levin, Hervatin, Koch-Weser, McCann, Sjoerdsma, "Potentiation of the antitumor therapeutic effects of 1,3-bis(2-chloroethyl)-1-nitrosourea by alpha-difluoromethylornithine, an ornithine decarboxylase inhibitor," *Cancer Res.*, 41(11 Pt 1):4426–4431, 1981.

Messing, Young, Hunt, Gilchrist, Newton, Bram, Hisgen, Greenberg, Kuglitsch, Wegenke, "Comparison of bladder cancer outcome in men undergoing hematuria home screening versus those with standard clinical presentations," *Urology*, 45(3):387–396, 1995.

Meyskens Jr. and Gerner, "Development of difluoromethylornithine as a chemoprevention agent for the management of colon cancer," *J. Cell Biochem. Suppl.*, 22:126–131, 1995.

Mimori, Mori, Shiraishi, Tanaka, Haraguchi, Uco, Shirasaka, Akiyoshi, "Expression of ormithine decarboxylase mRNA and c-myc mRNA in breast tumours," *Int. J Oncol.*, 12(3):597–601, 1998.

Muller, Afra, Schroder, "Supratentorial recurrences of gliomas. Morphological studies in relation to time intervals with astrocytomas," *Acta Neurochir* (Wien), 37:75–91, 1977.

Nelson, Tsukada, Schoenfeld, Fulling, Lamarche, Peress, "Necrosis as a prognostic criterion in malignant supratentorial, astrocytic gliomas," *Cancer*, 52:550–554, 1983.

Oredsson, Pegg, Alhonen-Hongisto, Deen, Marton, "Possible factors in the potentiation of 1-(2-chloroethyl)-3-trans-4-methylcyclohexyl-1-nitrosourea cytotoxicity by alpha-difluoromethylornithine in 9L rat brain tumor cells," *Eur. J Cancer Clin. Oncol.*, 20(4):535–542, 1984.

Pasic, Heisey, Love, "α-difluoromethylornithine ototoxicity. Chemoprevention clinical trial results," *Arch. Otolaryngol Head Neck Surg.*, 1123(12): 1281–1286, 1997.

Pegg and McCann, "Polyamine metabolism and function," *Am. J Physiol.*, 243(5):C212–C221, 1982.

Pegg, "Recent advances in the biochemistry of polyamines in eukaryotes," *Biochem.*, 234(2):249–262, 1986.

Porter, Herrera-Omelas, Pera, Petrelli, Mittelman, "Polyamine biosynthetic activity in normal and neoplastic human colorectal tissues," *Cancer*, 60(6):1275–1281, 1987.

Prados, Rodriguez, Chamberlain, Silver, Levin, "Treatment of recurrent gliomas with 1,3-bis(2-chloroethyl)-1-nitrosourea and alpha-difluoromethylornithine," *Neurosurgery*, 24(6):806–809, 1989.

Sano, Deen, Oredsson, Marton, "Effects of alpha-difluoromethylornithine on the growth of 9L rat brain tumor multicellular spheroids and their response to 1,3-bis(2-chloroethyl)-1-nitrosourea," *Cancer Res.*, 44(2):577–581, 1984.

Sarkar, Dolan, Gonzalez, Marton, Pegg, Deen, "The effects of O6-benzylguanine and hypoxia on the cytotoxicity of 1,3-bis(2-chloroethyl)-1-nitrosourea in nitrosourea-resistant SF-763 cells," *Cancer Chemother. Pharmacol.*, 32(6):477–481, 1993.

Scalabrino and Ferioli, "Degree of enhancement of polyamine biosynthetic decarboxylase activities in human tumors: a useful new index of degree of malignancy," *Cancer Detect. Prev.*, 8(1–2):11–16, 1985.

Scalabrino, Modena, Ferioli, Puerari, Luccarelli, "Degrees of malignancy in human primary central nervous system tumors: ornithine decarboxylase levels as better indicators than adenosylmethionine decarboxylase levels," *J. Natl. Cancer Inst.*, 68(5):751–754, 1982.

Seidenfeld and Komar, "Chemosensitization of cultured human carcinoma cells to 1,3-bis(2-chloroethyl)-1-nitrosourea by difluoromethylornithine-induced polyamine depletion," *Cancer Res.*, 45(5):2132–2138, 1985.

Shaw, Scheithauer, O'Fallon JR, Davis, "Mixed oligoastrocytomas: a survival and prognostic factor analysis," *Neurosurgery*, 34:577–582, 1994.

Takami, Koudaira, Kodaira, "Relationship of ornithine decarboxylase activity and human colon tumorigenesis," *Jpn. J. Clin. Oncol.*, 24(3):141–143, 1994.

Thet, Parra, Shelburne, "Repair of oxygen-induced lung injury in adult rats. The role of ornithine decarboxylase and polyamines," *Am. Rev. Respir. Dis.*, 129(1):174–181, 1984.

Thomas, Kiang, Janne, Thomas, "Variations in amplification and expression of the ornithine decarboxylase gene in human breast cancer cells," *Breast Cancer Res. Treat.*, 19(3):257–267, 1991.

Wacker, Hoshino, Ahn, Davis, Prados," "The prognostic implications of histologic classification and bromodeoxyuridine labeling index of mixed gliomas," *J. Neuro-Oncology*, 19:113–122, 1994.

Williams-Ashman and Canellakis, "Polyamines in mammalian biology and medicine," *Perspect. Biol. Med.*, 22(3): 421–453, 1979.

TABLE 1

Patient Characteristics for Anaplastic Glioma Strata

|  | DFMO + PCV Arm | PCV Arm |
|---|---|---|
| Number | 124 | 123 |
| Female Patients | 39% | 44% |
| Median age (range), years | 41.8 (22–73) | 41.4 (22–76) |
| Karnofsky Score: | 90.8 | 89.4 |
| Median RT dose (range) | 59.5 Gy (48.6–72.2) | 59.6 Gy (45–69.8) |
| Weeks, diagnosis to registration | 17.2 (median 13.1) | 17.5 (median 13.4) |
| Surgery: Biopsy | 44 (36%) | 39 (32%) |
| Subtotal resection | 51 (41%) | 52 (42%) |
| Gross total resection | 29 (23%) | 32 (26%) |

TABLE 2

Patient Characteristics for Anaplastic Glioma Strata

|  | PCV/DFMO (%) | PCV |
|---|---|---|
| Anaplastic astrocytoma | 94 (75.8) | 86 (69.9) |
| Anaplastic oligoastrocytoma | 4 (3.2) | 8 (6.5) |
| Anaplastic oligodendroglioma | 17 (13.7) | 24 (19.5) |
| Anaplastic glioma | 5 (4) | 3 (2.4) |
| Oligodendroglioma | 2 (1.6) | 2 (1.6) |
| Anaplastic ependymoma | 2 (1.6) | 0 (0) |

TABLE 3

Patient Characteristics for "Non-evaluable" Anaplastic Glioma Strata

|  | PCV/DFMO | PCV |
|---|---|---|
| Ineligible history | 4 | 2 |
| Refused treatment | 2 | 2 |
| Lost to follow |  | 1 |
| <6 days chemo | 2 | 2 |
| >6 and <14 days chemo | 3 | 3 |

TABLE 4

Patient Characteristics for "Best Evaluable" Anaplastic Gliomas

|  | DFMO + PCV Arm | PCV Arm |
|---|---|---|
| Number | 113 | 113 |
| Female Patients | 39% | 44% |
| Median age (range), years | 41.4 | 43.5 |
| Karnofsky Score: | 91.0 | 90.1 |
| Median RT dose (range) | 59.6 Gy (48.6–72.2) | 59.0 Gy (45–69.8) |
| Weeks, diagnosis to registration | 17.2 (median 13.1) | 17.5 (median 13.4) |
| Surgery: Biopsy | 38 (34%) | 33 (29%) |
| Subtotal resection | 48 (42%) | 48 (42%) |
| Gross total resection | 27 (24%) | 32 (28%) |

What is claimed is:

1. A method of treating anaplastic glioma in a subject comprising administering to said subject, in combined amount to effect treatment, a treatment regiment comprising at least one cycle of eflomithine, matulane and a nitrosourea.

2. The method of claim 1, wherein said nitrosurea is lomustine or carmustine.

3. The method of claim 1, further comprising vincristine.

4. The method of claim 3, wherein said treatment regimen comprises at least one cycle of eflomithine, lomustine, matulane and vincristine administration.

5. The method of claim 4, wherein said treatment regimen comprises administering eflomithine to said subject multiple times within said treatment cycle.

6. The method of claim 4, wherein said treatment regimen comprises administering eflomithine to said subject prior to lomustine, matulane or vincristine within said treatment cycle.

7. The method of claim 4, wherein said treatment regimen comprises administering eflornithine to said subject after lomustine, matulane or vincristine within said treatment cycle.

8. The method of claim 5, wherein said treatment regimen comprises administering eflomithine to said subject prior to and after lomustine, matulane and vincristine within said treatment cycle.

9. The method of claim 4, wherein said treatment regimen comprises administering vincristine to said subject multiple times within said treatment cycle.

10. The method of claim 4, wherein said treatment regimen comprises administering matulane to said subject multiple times within said treatment cycle.

11. The method of claim 4, wherein said treatment regimen comprises a daily oral dose of eflornithine of about 9.0 g/m² given in three equal administrations each eight hours.

12. The method claim 4, wherein said treatment regimen comprises a daily intravenous dose of vincristine of about 1.4 to about 2.0 mg/m².

13. The method of claim 4, wherein said treatment regimen comprises a daily oral dose of matulane of about 60 mg/m².

14. The method of claim 4, wherein said treatment regimen comprises a daily oral dose of lomustine of about 110 mg/m².

15. The method of claim 4, wherein said cycle comprises:

eflornithine administered on days 1 to 14 and days 43 to 56;

lomustine administered on day 15;

matulane administered on days 22–35; and vincristine administered on days 22 and 42.

16. The method of claim 15, wherein said cycle is repeated at eight week intervals for a total of six or seven cycles.

17. The method of claim 16, wherein said doses of one or more of eflomithine, lomustine, matulane and vincristine are modified after the first cycle.

18. The method of claim 1, wherein said subject has previously received radiation therapy.

19. The method of claim 4, wherein said subject has previously received chemotherapy in addition to eflomithine, lomustine, matulane and vincristine.

20. The method of claim 19, wherein said chemotherapy is hydroxyurea therapy.

21. The method of claim 20, further comprising radiation therapy during said hydroxyurea therapy.

22. The method of claim 16, wherein said subject is evaluated for neurotoxicity after each cycle.

23. The method of claim 16, wherein said subject is evaluated for ototoxicity after each cycle.

24. The method of claim 16, wherein said subject is evaluated for blood count and platelet count during and after each cycle.

25. The method of claim 1, wherein said subject has serum glutamic pyruvic transaminase and alkaline phosphatase less than or equal to two times normal values, total bilirubin less than or equal to 1.5 mg/dl, absolute neutrophil count of greater than or equal to 1500/mm³ and platelet count of greater than or equal to 125,000/mm³.

26. The method of claim 1, wherein eflornithine is L-eflomithine.

27. The method of claim 1, wherein eflornithine is D-eflornithine.

28. The method of claim 1, wherein eflornithine is a racemic mixture of L- and D-eflornithine.

29. A method of inhibiting the progression of anaplastic glioma in a subject comprising administering to said subject, in combined amount to effect treatment, a treatment regimen comprising at least one cycle of eflornithine, lomustine, matulane and vincristine administration.

30. The method of claim 29, where said treatment regimen is provided after radiation therapy.

31. A method of extending the life of a subject having anaplastic glioma comprising administering to said subject, in combined amount to effect treatment, a treatment regimen comprising at least one cycle of eflornithine, lomustine, matulane and vincristine administration.

32. The method of claim 31, where said treatment regimen is provided after radiation therapy.

33. A method of enhancing the effects of lomustine, matulane and vincristine on anaplastic glioma comprising administering to a patient having anaplastic glioma an amount of eflornithine sufficient to enhance the effects of lomustine, matulane and vincristine on said anaplastic glioma.

* * * * *

UNITED STATES PATENT AND TRADEMARK OFFICE
CERTIFICATE OF CORRECTION

PATENT NO.    : 6,653,351 B2
DATED         : November 25, 2003
INVENTOR(S)   : Victor A. Levin It is certified that error appears in the above-identified patent and that said Letters Patent is hereby corrected as shown below:

Title page,
Item [57], ABSTRACT,
Line 2, delete "eflomithine" and insert -- eflornithine -- therefor.

Column 19,
Lines 2, 7, 10, 13 and 21, delete "eflomithine" and insert -- eflornithine -- therefor.

Column 20,
Lines 2, 8 and 26, delete "eflomithine" and insert -- eflornithine -- therefor.

Signed and Sealed this

Twenty-seventh Day of April, 2004

JON W. DUDAS
*Acting Director of the United States Patent and Trademark Office*